United States Patent
Burdeniuc et al.

(10) Patent No.: US 10,421,832 B2
(45) Date of Patent: *Sep. 24, 2019

(54) LOW EMISSIONS POLYURETHANE FOAM MADE WITH ISOCYANATE REACTIVE AMINE CATALYSTS

(71) Applicant: EVONIK DEGUSSA GMBH, Essen (DE)

(72) Inventors: Juan Jesus Burdeniuc, Colmar, PA (US); Torsten Panitzsch, Henstedt-Ulzburg (DE); Renee Jo Keller, Orwigsburg, PA (US)

(73) Assignee: Evonik Degussa GmbH, Essen (DE)

( * ) Notice: Subject to any disclaimer, the term of this patent is extended or adjusted under 35 U.S.C. 154(b) by 103 days.

This patent is subject to a terminal disclaimer.

(21) Appl. No.: 15/510,328

(22) PCT Filed: Sep. 11, 2015

(86) PCT No.: PCT/US2015/049655
§ 371 (c)(1),
(2) Date: Mar. 10, 2017

(87) PCT Pub. No.: WO2016/040783
PCT Pub. Date: Mar. 17, 2016

(65) Prior Publication Data
US 2017/0247495 A1    Aug. 31, 2017

Related U.S. Application Data

(60) Provisional application No. 62/049,568, filed on Sep. 12, 2014.

(51) Int. Cl.
| | |
|---|---|
| C08G 18/18 | (2006.01) |
| C07C 209/48 | (2006.01) |
| C07C 253/30 | (2006.01) |
| C08G 18/76 | (2006.01) |
| C07C 211/14 | (2006.01) |
| C08G 18/48 | (2006.01) |
| C08G 18/66 | (2006.01) |
| C08G 18/32 | (2006.01) |
| C08G 18/40 | (2006.01) |
| C08G 18/08 | (2006.01) |
| C08J 9/00 | (2006.01) |
| C08G 101/00 | (2006.01) |

(52) U.S. Cl.
CPC ........ *C08G 18/1808* (2013.01); *C07C 209/48* (2013.01); *C07C 211/14* (2013.01); *C07C 253/30* (2013.01); *C08G 18/0871* (2013.01); *C08G 18/14* (2013.01); *C08G 18/1825* (2013.01); *C08G 18/3275* (2013.01); *C08G 18/409* (2013.01); *C08G 18/4804* (2013.01); *C08G 18/4812* (2013.01); *C08G 18/4841* (2013.01); *C08G 18/6688* (2013.01); *C08G 18/7621* (2013.01); *C08G 18/7657* (2013.01); *C08G 18/7671* (2013.01); *C08J 9/0061* (2013.01); *C08G 2101/005* (2013.01); *C08G 2101/0008* (2013.01); *C08G 2101/0083* (2013.01); *C08J 2205/05* (2013.01); *C08J 2205/06* (2013.01); *C08J 2375/08* (2013.01)

(58) Field of Classification Search
None
See application file for complete search history.

(56) References Cited

U.S. PATENT DOCUMENTS

| | | | |
|---|---|---|---|
| 4,049,591 | A | 9/1977 | McEntire et al. |
| 4,101,470 | A | 7/1978 | McEntire |
| 4,248,930 | A | 2/1981 | Haas et al. |
| 4,929,646 | A | 5/1990 | Nichols et al. |
| 5,688,837 | A | 11/1997 | Chao et al. |
| 5,859,079 | A | 1/1999 | Mercando et al. |
| 6,136,879 | A | 10/2000 | Nishida et al. |
| 6,596,663 | B1 | 7/2003 | Tamano et al. |
| 6,858,654 | B1 | 2/2005 | Wendel et al. |
| 6,924,321 | B2 | 8/2005 | Casati et al. |
| 8,367,870 | B2 | 2/2013 | Burdeniuc et al. |
| 8,552,078 | B2 | 10/2013 | Vedage et al. |
| 2004/0102535 | A1 | 5/2004 | Casati et al. |
| 2005/0014858 | A1 | 1/2005 | Choi et al. |
| 2006/0135634 | A1 | 6/2006 | Guidetti |
| 2008/0090922 | A1 | 4/2008 | Vedage et al. |
| 2011/0009512 | A1 | 1/2011 | Grigsby, Jr. et al. |
| 2013/0190415 | A1 | 7/2013 | Burdeniuc et al. |
| 2013/0243986 | A1 | 9/2013 | Girotti et al. |
| 2014/0073712 | A1* | 3/2014 | Otero Martinez ........... C08G 18/6564 521/137 |
| 2016/0075817 | A1 | 3/2016 | Burdeniuc et al. |

FOREIGN PATENT DOCUMENTS

| | | |
|---|---|---|
| EP | 0025142 A1 | 8/1980 |
| JP | 55420099 A | 2/1979 |

(Continued)

*Primary Examiner* — John M Cooney
(74) *Attorney, Agent, or Firm* — Andrew H. Chung; Linda S. Li; Jason S. Ngui

(57) ABSTRACT

Tertiary amine catalysts having isocyanate reactive groups capable of forming thermally stable covalent bonds able to withstand temperatures from 120° C. and higher and up to 250° C. are disclosed. These catalyst can be used to produce polyurethane foam having the following desirable characteristics: a) very low chemical emissions over a wide range of environmental conditions and isocyanate indexes (e.g., indexes as low as 65 but higher than 60); b) sufficient hydrolytic stability to maintain the catalyst covalently bound to foam without leaching of tertiary amine catalyst when foam is exposed to water or aqueous solutions even at temperatures higher than ambient (temperature range 25° C. to 90° C.); and c) stable contact interface between the polyurethane polymer and other polymers (for example polycarbonate) with minimal migration of tertiary amine catalyst from polyurethane polymer to other polymers yielding no noticeable polymer deterioration at the point of contact even under conditions of heat and humidity.

10 Claims, 2 Drawing Sheets

(56) References Cited

FOREIGN PATENT DOCUMENTS

| | | |
|---|---|---|
| JP | 2001181363 A | 7/2001 |
| WO | 0158976 A1 | 8/2001 |
| WO | 03016372 A1 | 2/2003 |
| WO | 03016373 A1 | 2/2003 |
| WO | 03055930 A1 | 7/2003 |
| WO | 2004060956 A1 | 7/2004 |
| WO | 2006116456 A1 | 11/2006 |

* cited by examiner

Fig 1: RATE OF RISE DATA FOR STANDARD CATALYSTS
DABCO®NE1070 AND AMINE-1
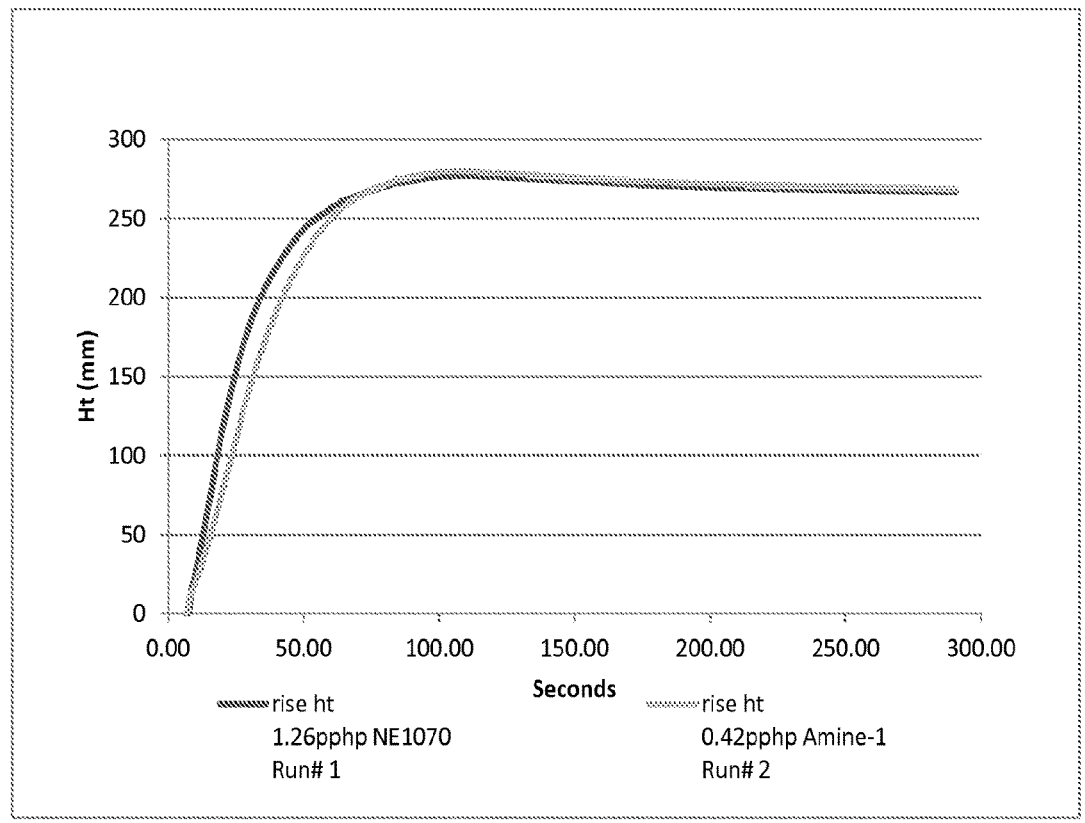
Figure 2: Experimental Set Up for Polycarbonate Stability
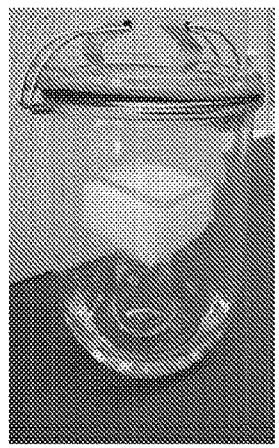

Figure 3: Appearance of Polycarbonate Plate After Being in Contact with PU Foam Made With Dabco®NE1070 Under Hot Humid Conditions
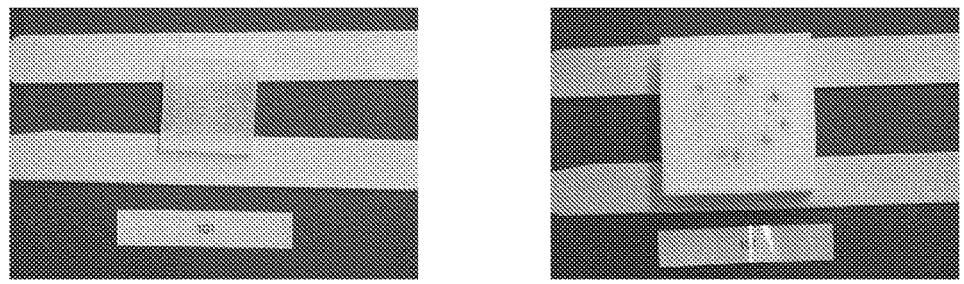
Figure 4: Appearance of Polycarbonate Plate After Being in Contact with PU Foam Made With Amine-1 Under Hot Humid Conditions
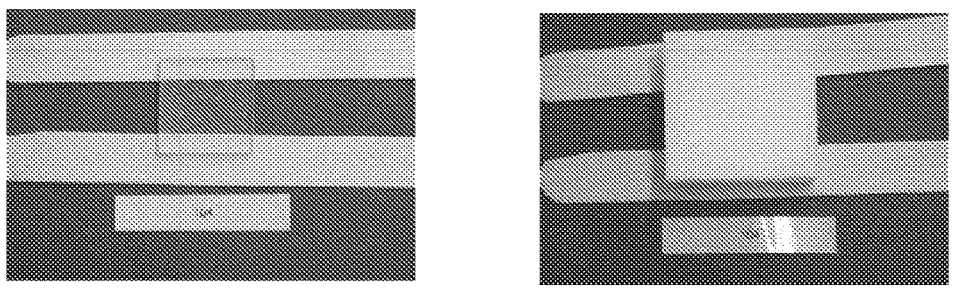

LOW EMISSIONS POLYURETHANE FOAM MADE WITH ISOCYANATE REACTIVE AMINE CATALYSTS

This Application claims the benefit of Application No. 62/049,568, filed on Sep. 12, 2014. The disclosure of Application No. 62/049,568 is hereby incorporated by reference.

FIELD OF THE INVENTION

The instant invention relates to tertiary amine catalysts having isocyanate reactive groups that are capable of forming thermally stable covalent bonds and withstanding temperatures from about 120° C. and higher and up to about 250° C. The instant invention also relates to using the inventive catalysts to produce polyurethane foam having the following desirable characteristics: a) very low chemical emissions over a wide range of environmental conditions and isocyanate indexes (e.g., indexes as low as about 65 but higher than about 60); b) sufficient hydrolytic stability to maintain the catalyst covalently bound to foam without leaching of tertiary amine catalyst when foam is exposed to water or aqueous solutions even at temperatures higher than ambient (e.g., temperature range about 25° C. to about 90° C.); and c) stable contact interface between the polyurethane polymer and other polymers (for example polycarbonate) with minimal migration of tertiary amine catalyst from polyurethane polymer to other polymers yielding no noticeable polymer deterioration at the point of contact even under conditions of heat and humidity.

BACKGROUND OF THE INVENTION

The production of open cell flexible polyurethane foam employs, a variety of additives and each one of them plays a role in determining the final characteristics and physical properties of the product. Although these additives represent a small percentage in the overall formulation and their emissions are expected to be relatively low, the increasing environmental demand for low volatile organic contents (VOC's) in finished products has placed additional requirements on additives to achieve these lower emissions while maintaining foam performance. There is a need in this art for additives with no emissions that can perform as well as the conventional less environmentally friendly standard products.

It is well known that conventional manufacturing procedures to make polyurethane foams use additives that are emissive. Tertiary amines such as triethylenediamine and bis(dimethylaminoethyl) ether are conventional emissive catalysts used by the industry to produce polyurethane foams.

One of the strategies used to reduce emissions from foam is based on introducing functional groups on tertiary amine catalysts able to react with isocyanate. Using this approach, the tertiary amine catalysts would remain covalently bonded to the polyurethane polymer preventing its release into the environment. This approach can have some limitations because the functionalized tertiary amine can react with isocyanate prematurely causing undesired side effects such as polymer chain termination which would result in poor physical properties, excessive cell opening or foam collapse or excessive cross linking which can result in extensive shrinkage and poor dimensional stability. Another alternative approach to reduce odor and emissions is based on utilizing materials with increasing molecular weight and/or polarity. Products such as dimethylaminopropyl urea, bis(dimethylaminopropyl) urea, bis(dimethylaminopropyl) amine and N,N-bis(dimethylaminopropyl)-N-(2-hydroxypropyl) amine can provide acceptable physical properties as compared to industry standards whereas most conventional reactive catalysts cannot always achieve today's consumer and manufacturer requirements. Using these catalysts can reduce significantly the overall emissions from foam. However, the finished articles produced are not typically emissions-free, and VOC and FOG values can reach several hundred ppm according to VDA 278 detection method. One key feature required for the isocyanate reactive tertiary amine catalyst relates to its ability to form a thermally stable covalent bond with the growing polyurethane polymer. The covalent bond should be stable enough to retain the amine catalyst in the polyurethane polymer when foam sample is heated and emissions are removed from the heated chamber by the constant flow of inert gas. Currently, there are a wide variety of functionalized amine polyurethane catalysts capable of reacting with isocyante during the polymerization process. However, in many cases foam produced with some of these reactive catalysts can still have amine emissions because the covalent chemical bonds that holds the amine catalysts into the polyurethane polymer are not sufficiently stable at the temperature of the test. Without wishing to be bound by any theory or explanation, it is believed that such emissions could result either in the release of the amine catalysts from the polyurethane polymer or in the release of by-products and chemical fragments from the thermal decomposition of the amine-polymer adduct.

In addition to thermal stability, these catalysts preferably form hydrolytically stable covalent bonds under a wide variety of conditions and pHs. Hydrolytic stability of the chemical bond between the tertiary amine and the polyurethane polymer plays an important role in applications where polyurethane foam is in contact with textiles that can be exposed to moisture and/or water or in applications where foam can directly be exposed to water while in contact with skin. If the hydrolytic stability of the chemical bond between the polymer and the tertiary amine is not sufficient then tertiary amine catalyst can leach from the polyurethane polymer and may allow amines to directly contact skin leading to skin irritation or skin sensitization.

Finally, thermal stability and catalyst immobilization at lower isocyanate index is an additional performance requirement. In addition to thermal stability at typical indexes such as 90-115 new catalyst need to be able to form covalent bonds with polyurethane polymer that have thermal stability and no emissions at indexes as low as 65 and typically higher than 60. This is a requirement that is difficult to meet because at low isocyanate index there is not sufficient NCO groups able to react with all OH groups from polyols and water so the new amine additive needs to be able to provide simultaneously sufficient catalytic activity to provide good quality foam and effectively compete with OH groups from polyols and water to become part of the polyurethane polymer and be retained in the polymer once the polymerization process is completed.

U.S. Pat. No. 5,859,079 disclosed a polyurethane catalyst composition that comprises N,N'-bis(3-dimethylaminopropyl)urea and 3-dimethylaminopropylurea. However when a cured polymer is heated to temperatures as high as 120° C. amine emissions can occur. In addition, water contacting foam produced using this catalyst can have an increased alkalinity.

U.S. Pat. No. 6,858,654 discloses a catalyst composition for promoting the polyurethane forming reaction which includes a gelling catalysts and a blowing catalyst The gelling catalyst are selected from tertiary aminoalkyl substituted primary or secondary amines and the blowing catalysts are selected from bis(aminoalkyl)ethers comprising alkanol moieties, primary amine moieties, or ureido moieties derived from such primary amine moieties. Foams produced with this catalyst can have a malodorous odor was well as polycarbonate staining capability.

U.S. Pat. No. 4,101,470 discloses compounds having a OH group able to react and form a covalent bond with isocyanate. Example of such composition can be obtained when reacting bis(dimethylaminopropyl)amine with propylene oxide to yield bis(3-dimethylaminopropyl)(2-hydroxypropyl)amine. One limitation of the composition and method disclosed is lack of thermal stability of the chemical bond as illustrated in the examples shown in U.S. Pat. No. 6,858,654 where 190 ppm decomposition products from bis(3-dimethylaminopropyl)(2-hydroxypropyl)amine is observed when foam is heated to 120° C. during testing according to VDA278 emissions test method.

U.S. Pat. No. 4,049,591 claims a method for producing a polyurethane foam which comprises reacting an organic polyisocyanate with an organic polyester polyol or polyether polyol in the presence of a catalytic amount of a compound having a general formula $[R''R''N—(CH_2)_3—]_2NCH_2CHRY$ where R" is a lower alkyl, R is hydrogen or lower alkyl and Y is selected from the groups consisting of CN, $CONH_2$, $CO_2R'$, $CONR_2'$ and $COR'$ where R' is independently H, lower alkyl or aryl. Limitations of these compounds includes emissions due to the lack of functionality able to react with NCO or inability to form thermally stable covalent bonds as well as hydrolytic instability.

The disclosure of the previously identified patents is hereby incorporated by reference.

There is a need in this art for foam made with polyurethane catalyst wherein the resultant foam passes emissions test. There is also a need in this art for catalysts that react with isocyanates and form thermally stable covalent bonds that are able to withstand the testing conditions that reflect extreme environmental conditions. Such a need can become a challenge as the isocyanate index is reduced to low levels (Index as low as 65 but higher than 60) because there is, stoichiometrically, an insufficient amount of NCO to react with all OH from polyol and water. In addition, the needed catalysts should be able to form hydrolytically stable covalent chemical bonds to prevent leaching of amine catalyst from the polyurethane article to avoid amine exposure to end users (e.g., when foam gets directly or indirectly in contact with humidity/moisture and heat). Moreover, the covalent bonds between tertiary amine catalysts and polyurethane polymer should be stable under extreme environmental conditions of heat and humidity such that in the event a polyurethane contacts other materials (for example polycarbonate in contact with polyurethane) the other materials are not damaged or deteriorated.

BRIEF SUMMARY OF THE INVENTION

The instant invention solves problems associated with conventional reactive catalysts and methods to reduce the amine emissions and in turn overall emissions from open cell flexible polyurethane foam. The instant invention also solves problems associated with catalyst leaching from foam during water contact and thereby avoiding the exposure of end users to amines. The invention also solves problems of material deterioration when certain materials are in contact with polyurethane polymer (e.g., problems that can be caused by catalyst migration in polyurethane foam during extreme environmental conditions of heat and humidity). The invention solves these problems while providing foam products with optimum physical properties and foam rate or rise kinetics.

The instant invention employs at least one tertiary amine gelling catalyst having a primary amine functionality in its structure in order to produce a polyurethane foam. In one aspect of the invention, the inventive gelling amine comprises N,N-bis(dimethylaminopropyl)-N-(3-aminopropyl)-amine having a chemical structure of $[Me_2N—(CH_2)_3]_2N—(CH_2)_3—NH_2$ wherein Me is $CH_3$ group.

The inventive gelling amine catalyst can provide the following benefits: a) elimination of emissions originating from the amine catalysts under rigorous conditions of temperature from about 120° C. and up to about 250° C.; b) formation of polyurethane polymers wherein the amine catalyst is retained in the polymer when exposed to humidity or water at various temperatures and pHs; c) minimal or no deterioration of other materials such as polycarbonate that come into contact with polyurethane polymer made with the catalyst of the invention; d) overall emission reduction on VOC and FOG when using the catalyst according to the invention; and e) significant reduction in use level of tertiary amine catalyst due to its high activity.

When using the catalyst of the invention the foam produced is characterized by: a) low to no amine emissions and reduced overall emissions as measured by the VDA 278 method; b) excellent physical properties such as tensile and tear strengths, compressions sets, ILDs, support factor and resilience; c) minimal or no deterioration of other materials such as polycarbonate that are in contact with polyurethane polymer; d) amines retained in polyurethane polymer by virtue of strong and thermally stable covalent bonds up to about 250° C.; e) sufficient hydrolytic stability that allows tertiary amine to be retained in polyurethane polymer when exposed to moisture or water at various temperatures and pHs; and f) significant reduction in gelling amine catalyst use level due to its high catalytic activity.

In one aspect of the invention, the amine catalyst of the invention can be used in combination with selected amine blowing catalysts such as at least one member selected from the group consisting of N,N,N'-trimethyl-N'-3-aminopropyl-bis(aminoethyl) ether or 2-[N-(dimethylaminoethoxyethyl)-N-methylamino]ethanol but more preferably with N,N,N'-trimethyl-N'-3-aminopropyl-bis(aminoethyl) ether.

Further aspect of the invention relates to a process for making polyurethane foams by using the inventive catalyst and to the resultant foams.

One aspect of the invention relates to a method for making a catalyst comprising contacting acrylonitrile and bis(dimethylaminopropyl)amine under conditions sufficient to obtain bis(dimethyleaminopropyl)-cyanoethyl-amine; and contacting bis(dimethyleaminopropyl)-cyanoethyl-amine with hydrogen under conditions sufficient to obtain N,N-bis(dimethylaminopropyl)-N-(3-aminopropyl)-amine.

Another aspect of the invention relates to a method for making a polyurethane foam comprising contacting at least one polyol and at least one polyisocyanate in the presence of a catalyst comprising N,N-bis(dimethylaminopropyl)-N-(3-aminopropyl)-amine.

Another aspect of the invention relates to a foam produced in accordance with any of the foregoing aspects wherein the foam is free from amine emissions when measured in accordance with VDA 278.

Another aspect of the invention relates to a foam produced in accordance with any of the foregoing aspects wherein the foam has improved physical properties.

The various aspect of the invention can be used alone or in combination.

BRIEF DESCRIPTION OF THE DRAWINGS

FIG. 1 is a graph showing the rate of rise v. time for a foam made in accordance with Example 3.

FIG. 2 is an illustration of a testing apparatus used in Example 5 for measuring deterioration to a polycarbonate surface in contact with a foam.

FIG. 3 is an illustration of a polycarbonate surface that was tested in accordance with Example 5.

FIG. 4 is an illustration of a polycarbonate surface that was tested in accordance with Example 5.

DETAILED DESCRIPTION OF THE INVENTION

The instant invention relates to an amine catalyst composition, methods for making and using the catalyst composition to make polyurethane foams. The inventive amine catalyst N,N-bis(dimethylaminopropyl)-N-(3-aminopropyl)-amine can be used to: a) minimize foam emissions without compromising foam physical properties (e.g., when measured in accordance with VDA-278); b) provide foam that are hydrolytically stable with no increase in pH on the aqueous phase when foam are exposed to water or moisture under various extreme environmental conditions; c) no damage to materials in contact to polyurethane as a result of catalyst not migrating out of the polyurethane polymer (for example when polycarbonate surfaces are exposed to polyurethane foam under various extreme conditions of temperature and humidity); d) optimum physical properties such as target density (ASTM 3574-A) with range of about 28 to about 80 kg/m$^3$, air flow (ASTM 3574-G) with range of about 40 to about 120 L/M, ILDs (indentation load deflection method ASTM 3574-B1) with range of about 150 to about 600N, support factor (ASTM 3574-61) with range of about 2.5 to about 3.5, preferably about 3, and resilience (ASTM 3574-H) range of about 40 to about 80%.

In one aspect of the invention a desirable foam has a Tensile/HA Tensile/Elongation/HA Elongation=DIN 53571—Range of about 80 to about 200%, a 50% Compression Set=ASTM D3574-D—Range of about 1 to about 20%, a HA Compression Set=ASTM D3574-J1 and J2—Range of about 5 to about 15%, and Tear=ASTM D3574-F—Range of about 150 to about 400.

The process according to the invention uses tertiary amine catalysts having the following chemical structure: [Me$_2$N—(CH$_2$)$_3$]$_2$N—(CH$_2$)$_3$—NH$_2$ wherein Me is CH$_3$ group. The inventive catalyst can be used in amounts ranging from about 0.1 pphp to about 20 pphp about 0.1 pphp to about 10 pphp and in some cases about 0.1 pphp to about 5 pphp. The inventive amine catalyst can be prepared by any suitable method. An example of a suitable method comprises reaction of acrylonitrile with bis(dimethylaminopropyl)amine to produce bis(dimethylaminopropyl)-cyanoethyl-amine followed by catalytic hydrogenation of the nitrile functionality to give N,N-bis(dimethylaminopropyl)-N-(3-aminopropyl)-amine. An example of a suitable method for making the inventive catalyst is described below in Example 1.

The inventive catalyst can be used to make foam with low chemical emissions, optimum physical properties, optimum foam rate or rise kinetics, significant amine emission reduction even at temperatures of about 120° C. and up to about 250° C., hydrolytically stable chemical bond between the tertiary amine gelling and the polyurethane polymer when foam is exposed to moisture or water at various temperatures and pHs as well as a relatively low use level when compared with other similar catalysts known in the art.

In one aspect of the invention, the inventive catalyst can be used as a gelling catalyst in combination with at least one blowing amine catalysts selected from the group consisting of N,N,N'-trimethyl-N'-3-aminopropyl-bis(aminoethyl) ether or 2-[N-(dimethylaminoethoxyethyl)-N-methylamino] ethanol, and typically N,N,N'-trimethyl-N'-3-aminopropyl-bis(aminoethyl) ether. The amount of blowing amine catalyst is typically about 0 pphp to about 5 pphp, about 0.01 pphp to about 2 pphp and in some cases about 0.05 pphp to about 1 pphp. These catalyst can be combined by any suitable method such as adding each separate catalysts to the premix or alternatively premixing both catalysts and adding the mixture of catalysts to the polyol premix.

The instant invention also relates to a process to make low or no amine emissions polyurethane foams using a combination of a selected group of isocyanate-reactive tertiary amines gelling catalysts in combination with catalysts of the invention, N,N-bis(dimethylaminopropyl)-N-(3-aminopropyl)-amine. The selected reactive gelling tertiary amines catalysts include any of the following functionalities urea, secondary-amine, primary amine, amides or secondary hydroxyl group. The combination of an isocyanate-reactive tertiary amine catalyst together with gelling catalyst N,N-bis(dimethylaminopropyl)-N-(3-aminopropyl)-amine of the invention produces foam with minimal emissions when compared with foam produced with any sole conventional emissive or non-emissive gelling catalyst described in the prior art. The % ratio of inventive catalyst to the foregoing gelling catalyst is typically about 100% to about 5% about 80% to about 10% and in some cases about 70% to about 20%. These catalyst can be combined by any suitable method such as such as adding each separate catalysts to the premix or alternatively premixing both catalysts and adding the mixture of catalysts to the polyol premix.

Preparation of Foams

Foams of any of the various types known in the art may be made using the methods of this invention, using typical polyurethane formulations to which have been added the appropriate amount of N,N-bis(dimethylaminopropyl)-N-(3-aminopropyl)-amine. For example, flexible open celled polyurethane foams with the excellent characteristics described herein will typically comprise the components shown below in Table I, in the amounts indicated. The components shown in Table I will be discussed in detail later below.

TABLE I

Polyurethane Components

| Component | Parts by Weight |
| --- | --- |
| Base Polyol | 20-100 |
| Polymer polyol | 0-80 |
| Silicone surfactant | 0.5-10 |
| Blowing agent | 2-4.5 |
| Crosslinker | 0.5-2 |
| Catalyst | 0.25-10 |
| Carboxylic acid (optional) | 0.05-3.0 |
| Polyisocyanate | To provide NCO index = 60-115 |

The amount of polyisocyanate used in polyurethane formulations according to the invention is not limited, but it will typically be within those ranges known to those of skill in the art. An exemplary range is given in table I, indicated by reference to "NCO Index" (isocyanate index). As is known in the art, the NCO index is defined as the number of equivalents of isocyanate, divided by the total number of equivalents of active hydrogen, multiplied by 100. The NCO index is represented by the following formula.

NCO index=[NCO/(OH+NH)]*100

Flexible foams typically use copolymer polyols as part of the overall polyol content in the foam composition, along with base polyols of about 4000-5000 weight average molecular weight and hydroxyl number of about 28-35. Base polyols and copolymer polyols will be described in detail later herein.

Catalysts

The catalysts of the present invention N,N-bis(dimethylaminopropyl)-N-(3-aminopropyl)-amine can be used as the sole gelling catalyst but alternatively the inventive catalysts can be used in combination with other tertiary amines containing isocyante reactive groups. Isocyanate reactive groups present in the alternative tertiary amine gelling co-catalyst consist essentially of primary amine, secondary amine, secondary-hydroxyl group, amide and urea. Examples of gelling catalysts comprise at least one member selected from the group consisting of N,N-bis(3-dimethyl-amino-propyl)-N-(2-hydroxypropyl) amine; N,N-dimethyl-N',N'-bis(2-hydroxypropyl)-1,3-propylenediamine; dimethylaminopropylamine (DMAPA); N-methyl-N-2-hydroxypropyl-piperazine, bis-dimethylaminopropyl amine (POLYCAT® 15), dimethylaminopropyl urea and N,N'-bis(3-dimethylaminopropyl) urea (DABCO® NE1060, DABCO® NE1070, DABCO® NE1080 and DABCO® NE1082), 1,3-bis(dimethylamino)-2-propanol, 6-dimethylamino-1-hexanol, N-(3-aminopropyl)imidazole, N-(2-hydroxypropyl)imidazol, N,N'-bis(2-hydroxypropyl) piperazine, N-(2-hydroxypropyl)-morpholine, and N-(2-hydroxyethylimidazole). The inventive catalyst as well as the foregoing catalyst combinations can be used with at least one blowing catalyst. Examples of blowing co-catalysts containing isocyanate reactive groups that can be used in combination with the above mentioned gelling catalysts include 2-[N-(dimethylaminoethoxyethyl)-N-methylamino]ethanol (DABCO® NE200), and N,N,N'-trimethyl-N'-3-aminopropyl-bis(aminoethyl) ether (DABCO® NE300).

The catalyst compositions may also include other components, for example transition metal catalysts such as organotin compounds or bismuth carboxylates for example when the desired polyurethane foam is a flexible slab stock. Metal catalyst can also comprise at least one member selected from the group consisting of dibutylin dilaureate, dimethyltin dilaureate, dimethyltin diacetate, dibutyltin diacetate, dimethyltin dilaurylmercaptide, dibutyltin dilaurylmercaptide, dimethyltin diisooctylmaleate, dibutyltin diisooctylmaleate, dimethyltin bi(2-thylhexyl mercaptacetate), dibutyltin bi(2-thylhexyl mercaptacetate), stannous octate, other suitable organotin catalysts, or a combination thereof. Other metals and salts thereof can also be included, such as, for example, bismuth (Bi). Suitable metal salts include carboxylate salts includes salts of pentanoic acid, neopentanoic acid, hexanoic acid, 2-ethylhexyl carboxylic acid, neohexanoic acid, octanoic acid, neooctanoic acid, heptanoic acid, neoheptanoic acid, nonanoic acid, neononanoic acid, decanoic acid, neodecanoic acid, undecanoic acid, neoundecanoic acid, dodecanoic acid, neododecanoic acid, and other suitable carboxylic acids. Other salts of transition metals of lead (Pb), iron (Fe), zinc (Zn) with pentanoic acid, neopentanoic acid, hexanoic acid, 2-ethylhexyl carboxylic acid, octanoic acid, neooctanoic acid, neoheptanoic acid, neodecanoic acid, neoundecanoic acid, neododecanoic acid, and other suitable carboxylic acids may also be included. The amount of metal catalyst and metal catalyst salts can range from about 0.01 to about 0.2, and about 0.1 to about 0.16.

While the inventive amine catalyst of the invention, N,N-bis(dimethylaminopropyl)-N-(3-aminopropyl)-amine, can be used with amines listed above, such usage can increase emissions from foam during the foam's useful lifetime as well as during foam manufacturing because the thermal stability of the chemical bonds between the isocyanate reactive co-catalysts are not as stable as the inventive catalyst. Typically, the loading of such emissive tertiary amine catalyst(s) for making foam according to the invention will be in the range of about 0.1 to about 20 pphp, more typically about 0.1 to about 10 pphp, and most typically about 0.1 to about 5 pphp. However, any effective amount may be used. The term "pphp" means parts per hundred parts polyol.

In one aspect, the inventive amines or a composition containing the inventive amines is acid blocked by being contacted with an acid. Suitable acids would include any organic carboxylic acids containing and saturated or unsaturated and substituted or unsubstituted aromatic group with single or multiple acids groups with or without isocyanate reactive groups. Examples if acids comprise formic acid, acetic acid, propionic acid, butanoic acid, pentanoic acid, hexanoic acid, pivalic acid, neopentanoic acid, neodecanoic acid, neododecanoic acid, 2-ethylhexanoic acid, glycolic acid, gluconic acid, salicylic acid, lactic acid, benzoic acid, phthalic acid, phthalic acid monoesters obtained from phthalic anhydride with glycols, polyacids such as polyacrylic acid, among others.

Organic Isocyanates

Suitable organic isocyanate compounds include, but are not limited to, hexamethylene diisocyanate (HDI), phenylene diisocyanate (PDI), toluene diisocyanate (TDI), and 4,4'-diphenylmethane diisocyanate (MDI). In one aspect of the invention, 2,4-TDI, 2,6-TDI, or any mixture thereof is used to produce polyurethane foams. Other suitable isocyanate compounds are diisocyanate mixtures known commercially as "crude MDI." One example is marketed by Dow Chemical Company under the name PAPI, and contains about 60% of 4,4'-diphenylmethane diisocyanate along with other isomeric and analogous higher polyisocyanates. While any suitable isocyanate can be used, an example of such comprises isocyanate having an index range from about 60 to about 120, in some cases about 60 to about 65 and typically from about 90 to about 110. The amount of isocyanate normally ranges from about 95 to about 105.

Polyol Component

Polyurethanes are produced by the reaction of organic isocyanates with the hydroxyl groups of polyol, typically a mixture of polyols. The polyol component of the reaction mixture includes at least a main or "base" polyol. Base polyols suitable for use in the invention include, as non-limiting examples, polyether polyols. Polyether polyols include poly(alkylene oxide) polymers such as poly(ethylene oxide) and poly(propylene oxide) polymers and copolymers with terminal hydroxyl groups derived from polyhydric compounds, including diols and triols. Examples of diols and triols for reaction with the ethylene oxide or propylene oxide include ethylene glycol, propylene glycol, 1,3-butanediol, 1,4-butanediol, 1,6-hexanediol, neopentyl glycol, diethylene glycol, dipropylene glycol, pentaerythritol, glycerol, diglycerol, trimethylol propane, and similar low molecular weight polyols. Other base polyol examples known in the art include polyhydroxy-terminated acetal resins, hydroxyl-terminated amines and hydroxyl-terminated polyamines. Examples of these and other suitable isocyanate-reactive materials may be found in U.S. Pat. No. 4,394,491; hereby incorporated by reference. Suitable polyether polyols also include those containing tertiary amine groups than can catalyze the gelling and the blowing reaction of polyurethanes, for example those described in U.S. Pat. No. 8,367,870; WO 03/016373 A1, WO 01/58976 A1; WO2004/060956 A1; WO03/016372 A1; and WO03/055930 A1; the disclosure of the foregoing US and WO publications is hereby incorporated by reference. Other useful polyols may include polyalkylene carbonate-based polyols and polyphosphate-based polyols.

In one aspect of the invention, a single high molecular weight polyether polyol may be used as the base polyol. Alternatively, a mixture of high molecular weight polyether polyols, for example, mixtures of di- and tri-functional materials and/or different molecular weight or different chemical composition materials may be used. Such di- and tri-functional materials include, but are not limited to polyethylene glycol, polypropylene glycol, glycerol-based polyether triols, trimethylolpropane-based polyether triols, and other similar compounds or mixtures.

In addition to the base polyols described above, or instead of them, materials commonly referred to as "copolymer polyols" may be included in a polyol component for use according to the invention. Copolymer polyols may be used in polyurethane foams to increase the resistance to deformation, for example to improve the load-bearing properties. Depending upon the load-bearing requirements, copolymer polyols may comprise from about 0 to about 80 percent by weight of the total polyol content. Examples of copolymer polyols include, but are not limited to, graft polyols and polyurea modified polyols, both of which are known in the art and are commercially available.

Graft polyols are prepared by copolymerizing vinyl monomers, typically styrene and acrylonitrile, in a starting polyol. The starting polyol is typically a glycerol-initiated triol, and is typically end-capped with ethylene oxide (approximately 80-85% primary hydroxyl groups). Some of the copolymer grafts to some of the starting polyol. The graft polyol also contains homopolymers of styrene and acrylonitrile and unaltered starting polyol. The styrene/acrylonitrile solids content of the graft polyol typically ranges from 5 wt % to 45 wt %, but any kind of graft polyol known in the art may be used.

Polyurea modified polyols are formed by the reaction of a diamine and a diisocyanate in the presence of a starting polyol, with the product containing polyurea dispersion. A variant of polyurea modified polyols, also suitable for use, are polyisocyanate poly addition (PIPA) polyols, which are formed by the in situ reaction of an isocyanate and an alkanolamine in a polyol.

Other suitable polyols that can be used according to the invention include natural oil polyols or polyols obtained from renewable natural resources such as vegetable oils. Polyols useful in the preparation of polyurethane foam from inexpensive and renewable resources are highly desirable to minimize the depletion of fossil fuel and other non-sustainable resources. Natural oils consist of triglycerides of saturated and unsaturated fatty acids. One natural oil polyol is castor oil, a natural triglyceride of ricinoleic acid which is commonly used to make polyurethane foam even though it has certain limitations such as low hydroxyl content. Other natural oils need to be chemically modified to introduce sufficient hydroxyl content to make them useful in the production of polyurethane polymers. There are two chemically reactive sites that can be considered when attempting to modify natural oil or fat into a useful polyol: 1) the unsaturated sites (double bonds); and 2) the ester functionality. Unsaturated sites present in oil or fat can be hydroxylated via epoxidation followed by ring opening or hydroformilation followed by hydrogenation. Alternatively, trans-esterification can also be utilized to introduce OH groups in natural oil and fat. The chemical process for the preparation of natural polyols using epoxidation route involves a reaction mixture that requires epoxidized natural oil, a ring opening acid catalyst and a ring opener. Epoxidized natural oils include epoxidized plant-based oils (epoxidized vegetable oils) and epoxidized animal fats. The epoxidized natural oils may be fully or partially epoxidized and these oils include soybean oil, corn oil, sunflower oil, olive oil, canola oil, sesame oil, palm oil, rapeseed oil, tung oil, cotton seed oil, safflower oil, peanut oil, linseed oil and combinations thereof. Animal fats include fish, tallow and lard. These natural oils are triglycerides of fatty acids which may be saturated or unsaturated with various chain lengths from C12 to C24. These acids can be: 1) saturated: lauric, myristic, palmitic, steric, arachidic and lignoceric; 2) mono-unsaturated: palmitoleic, oleic, 3) poly-unsaturated: linoleic, linolenic, arachidonic. Partially or fully epoxidized natural oil may be prepared when reacting peroxyacid under suitable reaction conditions. Examples of peroxyacids utilized in the epoxidation of oils have been described in WO 2006/116456 A1; hereby incorporated by reference. Ring opening of the epoxidized oils with alcohols, water and other compounds having one or multiple nucleophilic groups can be used. Depending on the reaction conditions oligomerization of the epoxidized oil can also occur. Ring opening yields natural oil polyol that can be used for the manufacture of polyurethane products. In the hydroformilation/hydrogenation process, the oil is hydroformylated in a reactor filled with a hydrogen/carbon monoxide mixture in the presence of a suitable catalyst (typically cobalt or rhodium) to form an aldehyde which is hydrogenated in the presence of cobalt or nickel catalyst to form a polyol. Alternatively, polyol from natural oil and fats can be produced by trans-esterification with a suitable poly-hydroxyl containing substance using an alkali metal or alkali earth metal base or salt as a transesterification catalyst. Any natural oil or alternatively any partially hydrogenated oil can be used in the transesterification process. Examples of oils include but are not limited to soybean, corn, cottonseed, peanut, castor, sunflower, canola, rapeseed, safflower, fish, seal, palm, tung, olive oil or any blend. Any multifunctional hydroxyl compound can also be used such as lactose, maltose, raffinose, sucrose, sorbitol, xylitol, erythritol, mannitol, or any combination.

Polyols amounts are defined by pphp. There are 3 types of polyols above defined: standard polyol or polyether polyol which can be used in the range of about 100 pphp (the only polyol) to about 10 pphp. The copolymer polyol (CPP) can be used in the range of about 0 to about 80 pphp. Finally the NOP (natural oil polyol) which typically can be present from about 0 to about 40 pphp.

In one aspect of the invention, at least one of the polyols has functionality of 3 to 5, 3 to 4 and in some cases 3 to 3.5. In another aspect of the invention, at least one of the polyols has an OH Number that ranges from about 15 to about 50.

Blowing Agents

Polyurethane foam production may be aided by the inclusion of a blowing agent (BA) to produce voids in the polyurethane matrix during polymerization. Any suitable blowing agent may be used. Suitable blowing agents include compounds with low boiling points which are vaporized during the exothermic polymerization reaction. Such blowing agents are generally inert or they have low reactivity and therefore it is likely that they will not decompose or react during the polymerization reaction. Examples of low reactivity blowing agents include, but are not limited to, carbon dioxide, chlorofluorocarbons (CFCs), hydrofluorocarbons (HFCs), hydrochlorofluorocarbons (HCFCs), fluoroolefins (FOs), chlorofluoroolefins (CFOs), hydrofluoroolefins (HFOs), hydrochlorfluoroolefins (HCFOs), acetone, and low-boiling hydrocarbons such as cyclopentane, isopentane, n-pentane, and their mixtures. Other suitable blowing agents include compounds, for example water, that react with isocyanate compounds to produce a gas. The amount of BA is typically from about 0 (water blown) to about 80 pphp. Water (blow foam by reacting with isocyanate making CO2) can be present in the range from about 0 (if a BA is included) to about 60 pphp (a very low density foam) and typically from about 1.0 pphp to about 10 pphp and, in some cases, from about 2.0 pphp to about 5 pphp.

Other Optional Components

A variety of other ingredients may be included in the formulations for making foams according to the invention. Examples of optional components include, but are not limited to, cell stabilizers, crosslinking agents, chain extenders, pigments, fillers, flame retardants, auxiliary urethane gelling catalysts, auxiliary urethane blowing catalysts, transition metal catalysts, alkali and alkali earth carboxylate salts and combinations of any of these.

Cell stabilizers may include, for example, silicone surfactants as well as organic anionic, cationic, zwiterionic or nonionic surfactants. Examples of suitable silicone surfactants include, but are not limited to, polyalkylsiloxanes, polyoxyalkylene polyol-modified dimethylpolysiloxanes, alkylene glycol-modified dimethylpolysiloxanes, or any combination thereof. Suitable anionic surfactants include, but are not limited to, salts of fatty acids, salts of sulfuric acid esters, salts of phosphoric acid esters, salts of sulfonic acids, and combinations of any of these. Suitable cationic surfactants include, but are not limited to quaternary ammonium salts (pH dependent or permanently charged) such as cetyl trimethylammonium chloride, cetyl pyridinium chloride, polyethoxylated tallow amine, benzalkonium chloride, benzethonium chloride and the like. Suitable zwiterionic or amphoteric surfactants include but are not limited to sultaines, aminoacids, imino acids, betaines and phosphates. Suitable non-ionic surfactants include but are not limited to fatty alcohols, polyoxyethylene glycol alkyl ethers, polyoxypropylene glycol alkyl ethers, glucosides (such as decyl, lauryl and octyl glucosides), polyoxyethylene glycol alkyl phenol ethers, glycol alkyl esters, and the like. Cell stabilizers can used in an amount from about 0.1 to about 20 pphp and typically from about 0.1 to about 10 pphp and, in some cases, from about 0.1 to about 5.0 pphp. Fire retardants can be used in an amount from about 0 to about 20 pphp and from about 0 to about 10 pphp and from about 0 to about 5 pphp.

Crosslinking agents include, but are not limited to, low-molecular weight compounds containing at least two moieties selected from hydroxyl groups, primary amino groups, secondary amino groups, and other active hydrogen-containing groups which are reactive with an isocyanate group. Crosslinking agents include, for example, polyhydric alcohols (especially trihydric alcohols, such as glycerol and trimethylolpropane), polyamines, and combinations thereof. Non-limiting examples of polyamine crosslinking agents include diethyltoluenediamine, chlorodiaminobenzene, diethanolamine, diisopropanolamine, triethanolamine, tripropanolamine, 1,6-hexanediamine, and combinations thereof. Typical diamine crosslinking agents comprise twelve carbon atoms or fewer, more commonly seven or fewer. Crosslinking agents can used in an amount from about 0.1 to about 20 pphp and typically from about 0.1 to about 10 pphp and, in some cases, from about 0.1 to about 5.0 pphp.

Examples of chain extenders include, but are not limited to, compounds having hydroxyl or amino functional group, such as glycols, amines, diols, and water. Specific non-limiting examples of chain extenders include ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof. Chain extenders can used in an amount from about 0.1 to about 100 pphp and typically from about 0.1 to about 50 pphp and, in some cases, from about 0.1 to about 5.0 pphp.

Pigments may be used to color code the polyurethane foams during manufacture, for example to identify product grade or to conceal yellowing. Pigments may include any suitable organic or inorganic pigments known in the polyurethane art. For example, organic pigments or colorants include, but are not limited to, azo/diazo dyes, phthalocyanines, dioxazines, and carbon black. Examples of inorganic pigments include, but are not limited to, titanium dioxide, iron oxides, or chromium oxide. The amount of pigment can range from about 0 pphp (no pigments added) to about 40 pphp.

Fillers may be used to increase the density and load bearing properties of polyurethane foams. Suitable fillers include, but are not limited to, barium sulfate or calcium carbonate. The amount of fillers can range from about 0 pphp (no fillers added) to about 40 pphp.

Flame retardants may be used to reduce the flammability of polyurethane foams. For example, suitable flame retardants include, but are not limited to, chlorinated phosphate esters, chlorinated paraffins, or melamine powders. Flame retardants can be used in an amount from about 0 to about 20 pphp and from about 0 to about 10 pphp and from about 0 to about 5 pphp.

In one aspect of the invention, the inventive catalyst is free or substantially free of certain amine catalysts. Examples of materials that can be excluded are amine catalysts having no isocyanate groups typically know as fugitive catalysts in particular when their use levels are >0.20 pphp and in some cases >0.10 pphp and in some cases >0.05 pphp as these materials are contributors to amine emissions. A list of examples of amines within this category include triethylenediamine (TEDA), N-methylimidazole, 1,2-dimethyl-imidazole, N-methylmorpholine, N-ethylmorpholine, triethylamine, N,N'-dimethyl-piperazine, 1,3,5-tris(dimethylaminopropyl)hexahydrotriazine, 2,4,6-tris(dimethylamino-methyl)phenol, N-methyldicyclohexylamine, pentamethyldipropylene triamine, N-methyl-N'-(2-dimethylamino)-ethyl-piperazine, tributylamine, pentamethyldiethylenetriamine, hexamethyltriethylenetetramine, heptamethyltetraethylenepentamine, dimethylamino-cyclohexylamine, pentamethyldipropylenetriamine, bis(dimethylaminoethyl)ether, tris(3-dimethylamino)propylamine, 1,8-diazabicyclo[5.4.0]undecene, or its acid blocked derivatives, and the like, as well as any mixture thereof.

Certain aspects of the invention are illustrated by the following Examples. These Examples are illustrative only and shall not limit the scope of any claims appended hereto. Foams were evaluated by using Handmix Evaluations or Machine Evaluations as described below.

EXAMPLES

Handmix Evaluations

Handmix experiments were conducted using the following procedure. Formulations were blended together for approximately 10 minutes using a mechanical mixer equipped with a 7.6 cm diameter high shear mixing blade, rotating at 5000 rpm. Premixed formulations were maintained at 23±1° C. using a low temperature incubator. Mondur TD-80 (an 80/20 2,4/2,6 isomer blend of toluene diisocyanate) or modified MDI was added to the premix at the correct stoichiometric amount for the reported index of each foam. The mixture was blended together with Premier Mill Corporation Series 2000, Model 89, and dispersed for approximately five seconds. The foaming mixture was transferred to an Imperial Bondware #GDR-170 paper bucket and allowed to free rise while data was recorded.

Machine Evaluations

Machine runs for the flexible molded foam were conducted on a Hi Tech Sure Shot MHR-50, cylinder displacement series and high-pressure machine. Fresh premixes, consisting of the appropriate polyols, water, crosslinker, surfactants and catalysts for each formulation were charged to the machine. Mondur TD-80 was used throughout the entire study. All chemical temperatures were held at 23±2° C. via the machine's internal temperature control units. Foam pours were made into an isothermally controlled, heated aluminum mold maintained at 63±2° C. The mold was a typical physical property tool designed with internal dimensions of 40.6 cm×40.6 cm×10.2 cm. The mold has five vents, each approximately 1.5 mm in diameter, centered in each corner 10.0 cm from each edge and the geometric center of the lid. The mold was sprayed with a solvent-based release agent, prior to every pour and allowed to dry for one minute before pouring. The foam premix was puddle poured into the center of the mold with a wet chemical charge weight capable of completely filling the mold and obtaining the desired core densities reported. Minimum fill requirements were established for each formulation evaluated. The foam article was demolded at 240 seconds (4 minutes) after the initial pour (detailed in next paragraph). Upon demold, the foam was placed through a mechanical crusher or tested for Force-to-Crush (FTC) measurements or allow to cool down to determine dimensional stability (detailed below).

Foam made with each catalyst set were mechanically crushed 1 minute after demold using a Black Brothers Roller crusher set to a gap of 2.54 cm. Crushing was conducted three times on each part, rotating the foam 90 degrees after each pass through the rollers. All parts produced for physical testing were allowed to condition for at least seven days in a constant temperature and humidity room (21±2° C., 50±2% relative humidity).

FTC measurements were conducted 45 seconds after demold. The pad was removed from the mold, weighed and placed in the FTC (force to crush) apparatus (model number ISCO HGI Pressure Pump). The force detection device is equipped with a 2.2 kg capacity pressure transducer mounted between the 323 cm$^2$ circular plate cross head and the drive shaft. The actual force is shown on a digital display. This device is operated in accordance with ASTM D-3574, Indentation Force Deflection Test and provides a numerical value of freshly demolded foam's initial hardness or softness. The pad was compressed to 50 percent of its original thickness at a cross-head velocity of 275 mm per minute with the force necessary to achieve the highest compression cycle recorded in Newton's. Ten compression cycles were completed. A cycle takes approximately 30 seconds to complete.

Example 1

Synthesis of N,N-Bis-(dimethylaminopropyl)-N-(3-aminopropyl)-amine (Amine-1)

In the first step, a 1000 ml stainless steel reactor was charged with 424 g of bis(dimethylaminopropyl) amine and 23 g of water. The reactor was purged with nitrogen, heated up to 75° C. and 126 g of acrylonitrile was slowly fed in the reactor over a period of 1.5 hours. After all acrylonitrile was transferred into the reactor the temperature was maintained at 75° C. for an additional 4.0 hours. The reaction mixture was allowed to cool down to 25° C. and the product was removed from the reactor and analyzed by GC giving 96% yield of desired product 2-cyanoethyl-bis(dimethylaminopropyl)amine. In the second step, a 1000 ml stainless steel reactor was charged with 198 g of isopropanol and 6.9 g of standard Raney-Cobalt catalyst. The reactor was purged with nitrogen three times and the temperature was increased to 120° C. The reactor was pressurized with 800 psi of hydrogen and cyanoethyl-bis(dimethylaminopropyl)amine (344 g) was fed in the reactor at a rate of about 100 ml per hour for a period of about 4 hours. Once transfer of cyanoethyl-bis(dimethylaminopropyl)amine was completed the temperature was increased to 130° C. and hold for one hour. The product was analyzed by GC yielding 93% of desired product N,N-bis-(dimethylaminopropyl)-N-(3-aminopropyl)-amine (Amine-1), and 5% bis(dimethylaminopropyl) amine, 1.5% N,N-bis-(dimethylaminopropyl)-N-(3-propylaminopropyl)-amine and 0.5% N,N-(bis-(3-(N,N-bis-(dimethylaminopropyl))-amino)-propyl)-amine.

Example 2

Physical Properties of PU Foam Made with Various Gelling Catalysts and their Comparison with Standard Catalysts Dimethylaminopropyl Urea, and bis(dimethylaminopropyl) urea Foam pads were prepared by adding a tertiary amine catalyst to about 302 g of a premix (prepared according to the formulation shown in Table II) in a 32 oz (951 ml) paper cup. The formulation was mixed for about 10 seconds at about 6,000 RPM using an overhead stirrer fitted with a 2-inch (5.1 cm) diameter stirring paddle. Toluene diisocyanate (TDI) was then added, and the formulation was mixed well for about another 6 seconds at about 6,000 RPM using the same stirrer, after which it was poured into a pre-heated mold at 70° C. and demolded after 4 minutes. The foam pads were removed from the mold, hand crushed, weighed and machine crushed at 75% pad thickness. Foam pads were stored under constant temperature and humidity conditions for 48 hours before being cut and tested.

TABLE II

FORMULATION COMPONENTS

| Component | PPHP |
|---|---|
| SPECFLEX ® NC 630[1] Polyol | 50 |
| SPECFLEX ® NC 700[2] Polyol | 50 |
| Water | 3.0 |
| DABCO ® DC6070[3] low emissions silicon surfactant | 0.60 |
| Catalyst[4] | Varied |
| Diethanolamine (crosslinker) | 0.70 |
| Toluene diisocyanate | To provide NCO index = 100 |

[1]High functionality capped polyether polyol of high molecular weight, functionality, and primary hydroxyl content with a base polyol molecular weight of about 5500, available from Dow Chemical Company, Midland, MI.
[2]Grafted polyether polyol containing copolymerized styrene and acrylonitrile, base polyol molecular weight about 4800, available from Dow Chemical Company, Midland, MI.
[3]Silicone surfactant is available from Air Products and Chemicals, Inc.
[4]The amine catalyst is available from Air Products and Chemicals, Inc.

This increase in height can also be displayed as a rate of changing height (a velocity) versus time. Useful comparisons can be made on the rate of the foaming reaction by recording the time required after mixing for the foam to reach a standard height (TOC=Top of the Cup), the maximum foam rise velocity, the time after mixing that was required to achieve the maximum velocity as well as the string gel time (SGT) which is the time at which the polymerizing mass is able to form polymer strings when touched with a wooden tongue suppressor.

Table III shows the list of catalysts evaluated in flexible open celled molded polyurethane foam pads. The flexible molded pads are made using a single gelling amine catalyst (no blowing catalysts were used in the foam examples of Table III) to show the influence of each individual catalyst chemical structure on the final physical properties. Desirable physical properties were obtained with triethylenediamine (TEDA). However, TEDA is an emissive catalyst unable to react with isocyanate thereby causing relatively high amine emissions in the finished product in detriment of overall quality (window fogging in cars, PVC staining, amine odor, etc). Among the catalysts with isocyanate reactive groups, Dabco®NE1070 is effective because of its optimum 50 compression sets, humid-aged tensile strength and comparable tensile, tear and elongation.

TABLE III

PHYSICAL PROPERTIES OF VARIOUS COMMON CATALYSTS

| Catalyst | Humid Aged Tensile Strength (Kpa) | 50% Compression Set | Tensile Strength (Kpa) | Elongation (%) | Tear (N/m) |
|---|---|---|---|---|---|
| Triethylenediamine (1) | 177 | 6 | 181 | 102 | 305 |
| Dimethylaminopropylureas (mono and bis mixture) (2) | 64 | 9 | 170 | 93 | 286 |
| N,N-bis(dimethylamino propyl)-N'-(2-hydroypropyl)amine (3) | 54 | 20 | 164 | 92 | 320 |
| N,N-dimethylaminopropyl-N'-(2-hydroxyethyl)-N'-methylamine (4) | 43 | 36 | 170 | 101 | 297 |
| Bis(dimethylaminopropyl) amine (5) | 17 | 17 | 162 | 97 | 298 |
| N,N-dimethylaminoethyl-N'-(2-hydroxyethyl)-N'-methylamine (6) | No mechanical integrity | 45 | 175 | 114 | 334 |

Example 3

Foam Rate of Rise Kinetics and Use Level Comparison for N,N-Bis-(dimethylaminopropyl)-N-(3-aminopropyl)-amine Foaming performance can be evaluated by comparing the foam height versus time for standards and new amine catalyst. Foam height profile can be measured by automated rate of rise equipment, utilizing free-rise cup foam samples with a FOMAT sonar rate-of-rise device (hereafter referred to as a "ROR"). The FOMAT device comprises a sonar sensor that measures and records the height in millimeters (mm) of the rising foam sample versus time in seconds (s), directly after mixing all components of the formulation. The FOMAT standard software generates both height versus time plots and velocity versus time plots. These plots are useful for comparing the relative reactivity of different catalyst formulations. Flexible open celled foam can be prepared by combining a total weight of about 300 g of the ingredients in Table II other than the isocyanate in a 32-oz (951 ml) paper cup. This premix formulation is then mixed for about 10 seconds at about 6,000 rpm using an overhead stirrer fitted with a 2-inch (5.1 cm) diameter stirring paddle. Sufficient toluene diisocyanate is then added to achieve the desired Isocyanate Index of about 100, and the formulation is mixed well for about another 6 seconds at about 6,000 rpm using the same stirrer. The cup is then placed under the FOMAT sensor. The start time for ROR measurement is automated for the FOMAT and begins directly after the end of the final mixing. Once the cup is placed under the ROR, the chemical mixture begins to polymerize. Since the walls of the cup restrict the expansion in all but the vertical direction, this expansion manifests itself in this experiment as an increase in height with passing time, as shown in FIG. 1.

TABLE IV

RATE OF RISE[1] DATA AND STRING GEL TIME

| Run # | Gel Catalyst | pphp | TOC[2] (sec) | SGT[2] (sec) |
|---|---|---|---|---|
| 1 | DABCO NE1070 | 1.26 | 33 | 62 |
| 2 | Amine-1 | 0.43 | 42 | 63 |
| 3 | Amine-1 | 0.50 | 36 | 56 |
| 4 | Amine-1 | 0.63 | 32 | <49 |

[1]Rate of rise data performed with only gelling catalyst DABCO ®NE1070 or Amine-1 (no blowing catalyst present in these experiments);
[2]TOC and SGT as defined above

Example 4

Physical Properties of Polyurethane Foam Made with N,N-Bis-(dimethylaminopropyl)-N-(3-aminopropyl)-amine Foam pads were prepared by adding a tertiary amine catalyst to about 302 g of a premix (prepared as in Table 2) in a 32 oz (951 ml) paper cup. The formulation was mixed for about 10 seconds at about 6,000 RPM using an overhead stirrer fitted with a 2-inch (5.1 cm) diameter stirring paddle. Toluene diisocyanate (TDI) was then added, and the formulation was mixed well for about another 6 seconds at about 6,000 RPM using the same stirrer, after which it was poured into a pre-heated mold at 70° C. and demolded after 4 minutes. The foam pads were removed from the mold, hand crushed, weighed and machine crushed at 75% pad thickness. Foam pads were stored under constant temperature (21° C.) and humidity (50% relative humidity) conditions for 48 hours before being cut and tested.

| Run# | Gel Cat | Gel Cat pphp | Blow Cat | Blow Cat Pphp | SG (sec) | Ext (sec) |
|---|---|---|---|---|---|---|
| 1 | NE1070 | 1.26 | None | 0.00 | 42 | 56 |
| 2 | NE1070 | 1.26 | None | 0.00 | 43 | 59 |
| 3 | NE1070 | 1.26 | None | 0.00 | 43 | 57 |
| 4 | NE1070 | 1.26 | None | 0.00 | 42 | 56 |
| 5 | Amine-1 | 0.50 | None | 0.00 | 48 | 60 |
| 6 | Amine-1 | 0.50 | None | 0.00 | 42 | 55 |
| 7 | Amine-1 | 0.50 | None | 0.00 | 44 | 57 |
| 8 | Amine-1 | 0.50 | None | 0.00 | 42 | 56 |

Mold data recorded on foam pads made with only gelling catalyst DABCO ®NE1070 or Amine-1 (no blowing catalyst present in these experiments)

TABLE V

PHYSICAL PROPERTIES AT AMBIENT DATA

| Property | Method | Conditions | Units | Standard: Dabco ®NE1070 | New: Amine-1 |
|---|---|---|---|---|---|
| Core Density | ASTM 3574-A | Ambient | Kg/m3 | 38 | 36 |
| Section Density | ASTM 3574-A | Ambient | Kg/m3 | 44 | 42 |
| Air Flow | ASTM 3574-G | Ambient | SCFM | 3.5 | 3.0 |
| ILD 25% | ASTM 3574-B1 | Ambient | N | 210 | 210 |
| ILD 65% | ASTM 3574-B1 | Ambient | N | 547 | 516 |
| ILD 25% R | ASTM 3574-B1 | Ambient | N | 172 | 177 |
| Support Factor | ASTM 3574-B1 | Ambient | Ratio | 2.60 | 2.45 |
| Resilience | ASTM 3574-H | Ambient | % | 51 | 52 |
| Tensile Strength | DIN 53571 | Ambient | kPa | 131 | 147 |
| Tensile Elongation | DIN 53571 | Ambient | % | 79 | 90 |
| Tear Strength | ASTM 3574-F | Ambient | N/m | 320 | 306 |
| 50% Comp. Set | ASTM D3574-D | 70° C. Dry Oven | % | 8.5 | 9.0 |

Foam pads physical properties made with only gelling catalyst DABCO ®NE1070 or Amine-1 (no blowing catalyst present in these experiments)

Table V shows the ambient physical properties of flexible molded polyurethane foam pads made with a commercially available standard tertiary amine catalyst having isocyanate reactive groups (i.e., Dabco®NE1070 catalyst) as well as the new isocyanate reacting gelling catalyst "Amine-1"; full chemical name: N,N-Bis(dimethylaminopropyl)-N-(3-aminopropyl)-amine. Table V shows that the ambient physical properties for both catalysts were very similar, providing, in both cases foam pads with excellent physical properties.

TABLE VI

HUMID AGED PHYSICAL PROPERTIES

| Property | Method | Conditions | Units | Standard: Dabco ®NE1070 | New: Amine-1 |
|---|---|---|---|---|---|
| HALLS | ISO-3386-1 | Volkswagen | % | −55 | −54 |
| Humid Aged Tensile Strength | DIN 53571 | Volkswagen | kPa | 42 | 42 |
| Humid Aged Elongation | DIN 53571 | Volkswagen | % | 45 | 40 |
| 50% HA Comp. Set | ASTM 3574-D | Volkswagen | % | 33 | 33 |

The humid ageing procedure used is as follows: place samples to be tested in a dry oven at 90° C. for 24 hours for drying. Once dried, age samples for 200 hours @ 90° C. and 100% relative humidity. Samples are then dried after ageing in a dry oven at 70° C. for 22 hours. Samples are removed from drying oven and allowed to equilibrate at ambient conditions before measuring physical properties.

The flexible molded pads were made using a single amine catalyst to show the influence of each individual structure on physical properties. The evaluation shows that new gelling catalyst N,N-Bis(dimethylaminopropyl)-N-(3-aminopropyl)-amine performs similarly to a standard reactive catalyst such as Dabco®NE1070 catalyst.

Example 5

Ageing of PU Foam Produced with N,N-Bis(dimethylaminopropyl)-N-(3-aminopropyl)-amine in Contact with a Polycarbonate Surface The stability of a polycarbonate surface was determined by placing a 4 cm×4 cm×4 mm polycarbonate plate (Makrolon GP Clear 099 4 mm thick with no anti-UV agent) in contact with a 4 cm×4 cm×5 cm piece of foam inside an approximate 4 litter glass jar having at the bottom approximately 300 ml of water. The jar was brought to temperature (90° C.) and the foam in contact with the polycarbonate plate was placed inside the jar on a built-in glass support at about 5 cm above the water level. The jar was then hermetically closed and placed in an oven conditioned at 90° C. for 6 days. Referring now to FIG. 2, FIG. 2 is an illustration of the jar having the plate and foam positioned therein for testing.

The foam for this test was prepared according to the formulation shown in Table VII (MDI flexible foam) made at an isocyanate index of 90 using foam samples made during a machine run for the flexible molded foam which were conducted using a Hi Tech Sure Shot MHR-50, cylinder displacement series and high-pressure machine as described above.

TABLE VII

FORMULATION FOR POLYCARBONATE TEST

| | Foam Sample Number | |
|---|---|---|
| Component | 1 pphp | 2 pphp |
| Caradol ® 28-03 ET[1] | 100 | 100 |
| Daltocel ® F442[2] | 1.3 | 1.3 |

TABLE VII-continued

FORMULATION FOR POLYCARBONATE TEST

| | Foam Sample Number | |
|---|---|---|
| Component | 1 pphp | 2 pphp |
| Diethanolamine | 0.6 | 0.6 |
| Water | 3.5 | 3.5 |
| Dabco ®2525[3] | 1.0 | 1.0 |
| N,N,N'-trimethyl-N'-3-aminopropyl-bis(aminoethyl) ether | 0.2 | 0.2 |
| Dabco ®NE1070[4] | 1.2 | |
| Amine-1 | | 0.6 |
| Zelunat ®8814[5] | Index 90 | Index 90 |

[1]Reactive trifunctional polyol with a nominal molecular weight of about 6000 hydroxyl value of 28 mgKOH/g commercially available from Shell Chemicals.
[2]A ethylene oxide capped polyether polyol commercially available from Huntsman.
[3]Silicone surfactant is available from Air Products and Chemicals, Inc.
[4]Amine catalyst is available from Air Products and Chemicals, Inc as defined above.
[5]Conventional MDI isocyanate The appearance of the polycarbonate plates after being exposed under hot-humidity to polyurethane foam made with Dabco®NE1070 and Amine-1 catalysts can be seen in FIGS. 3 and 4 respectively. Also shown in FIG. 3 and FIG. 4 are the appearance of the foam surface on which the polycarbonate plate rested while being test. The foam made with "amine-1" appeared unchanged while the foam being in contact with foam made with Dabco®NE1070 appeared damaged and stained. The damaged caused on the surface of the polycarbonate specimen is a clear indication of amine catalyst leaching away from the polyurethane foam specimen and reaching the polycarbonate surface. This effect is clearly minimal when amine-1 is used as catalyst.

The extent of the surface damage on the polycarbonate plate can be monitored by measuring the weight loss of the specimen. Specimens with less surface damage experience less weight loss as shown in Table VIII. Thus, polycarbonate plate exposed under this testing condition with foam 2 made with Amine-1 have less mass loss than the polycarbonate plate exposed to foam 1 made with standard amine catalyst Dabco®NE1070.

TABLE VIII

FORMULATION FOR POLYCARBONATE TEST

| Sample | Δmg | % Mass Change | Foam Surface |
|---|---|---|---|
| Blank PC Plate | 16.4 | 0.34 | NA |
| 1 | −355.9 | −7.44 | Sticky and stained |
| 2 | 15.5 | 0.32 | Non-sticky |

Δmg = final mass-initial mass and % Mass Change = final mass-initial mass/initial mass.
Blank PC Plate = a control polycarbonate plate that was exposed to the hot humidity without being in contact with any polyurethane surface Example 6

Emissions Measured on Foam Made with Standard Reactive Amine Amine Catalysts and with new amine N,N-Bis(dimethylaminopropyl)-N-(3-aminopropyl)-amine at Low Isocyanate Index Machine foam pads were prepared as described above using a Hi Tech Sure Shot MHR-50, cylinder displacement series and high-pressure machine with a calculated isocyanate index of 65. These foam samples were used for the thermal desorption emissions study which were done following the formulations 1 and 2 shown in Table VIII.

TABLE VIII

FORMULATION FOR VDA278 EMMISION TEST

| | Foam Sample Number | |
|---|---|---|
| Component | 1 pphp | 2 pphp |
| Lupranol ®2095[1] | 85 | 85 |
| Lupranol ®4003/1[2] | 15 | 15 |
| Diethanolamine | 1.2 | 1.2 |
| Water | 3.0 | 3.0 |
| Dabco ®DC6070[3] | 1.0 | 1.0 |
| N,N,N'-trimethyl-N'-3-aminopropyl-bis(aminoethyl) ether | 0.2 | 0.2 |
| Dabco ®NE1070[4] | 1.2 | — |
| Amine-1 | — | 0.6 |
| Lupranat ®T-80[5] | Index 65 | Index 65 |

[1]Reactive trifunctional polyol hydroxyl value of 35 mgKOH/g commercially available from BASF.
[2]A high filled copolymer polyol for high resilience flexible foam with an hydroxyl number of 20 mgKOH/g and a solid content of 45%.
[3]Silicone surfactant is available from Air Products and Chemicals, Inc.
[4]Amine catalyst is available from Air Products and Chemicals, Inc as defined above.
[5]Conventional TDI mixture with 80% 2,4-toluenediisocyanate and 20% 2,6-toluenediisocyanate with NCO content of 48% commercially available from BASF.

TABLE IX

EMISSIONS RESULTS USING VDA278 METHOD

| | Emission | | | |
|---|---|---|---|---|
| | VOC | | FOG | |
| | Type | | | |
| | Total | Amine | Total | Amine |
| | Units | | | |
| | ppm | ppm | ppm | ppm |
| Foam sample 1 | 65 | 4 | 113 | 86 |
| Foam sample 2 | 61 | 0 | 36 | 0 |

Emission from foam shown in Table IX were measured using thermodesorption analysis and the substances emitted at 90° C. (VOC) and 120° C. (FOG) were quantified according to VDA 278 method. For this purpose a sample of the test material is conditioned to the corresponding temperature under the flow of inert gas, and the substances released are frozen out in the refrigerated injector of the gas chromatograph. The mixture is then passed through the gas chromatographic column and the total emissions quantified. The VOC and FOG are measured with the same sample. Quantification of the gaseous emissions (VOC) is made against an external toluene standard while the condensable emissions (FOG) are quantified against hexadecane ($C_{16}$-n-alkane). The concentrations are reported in ppm as total emissions in toluene and hexadecane equivalents. As shown in Table IX no amine emissions were detected in foam sample 2 made with amine-1 N,N-Bis-(dimethylaminopropyl)-N-(3-aminopropyl)-amine.

Example 7

Physical Properties of MDI Polyurethane Foam Made with N,N-Bis-(dimethylaminopropyl)-N-(3-aminopropyl)-amine at Index 105

Machine made foam pads were prepared according to the procedure described above according to the formulation shown in Table X at an isocyanate index of 105 to determine the performance of N,N-Bis-(dimethylaminopropyl)-N-(3-aminopropyl)-amine in comparison to Dabco®NE1070 in the presence of Dabco®NE300 as standard blowing catalyst.

TABLE X

FORMULATION FOR PHYSICAL PROPERTIES

| | Foam Sample Number | |
|---|---|---|
| Component | 1 pphp | 2 pphp |
| Caradol ® 28-03 ET[1] | 100 | 100 |
| Daltocel ® F442[2] | 1.3 | 1.3 |
| Diethanolamine | 0.6 | 0.6 |
| Water | 3.5 | 3.5 |
| Dabco ®2525[3] | 1.0 | 1.0 |
| N,N,N'-trimethyl-N'-3-aminopropyl-bis(aminoethyl) ether | 0.2 | 0.2 |
| Dabco ®NE1070[4] | 1.2 | |
| Amine-1 | | 0.6 |
| Zelunat ®8814[5] | Index 105 | Index 105 |

[1]Reactive trifunctional polyol with a nominal molecular weight of about 6000 hydroxyl value of 28 mgKOH/g commercially available from Shell Chemicals.
[2]A ethylene oxide capped polyether polyol commercially available from Huntsman.
[3]Silicone surfactant is available from Air Products and Chemicals, Inc.
[4]Amine catalyst is available from Air Products and Chemicals, Inc as defined above.
[5]Conventional MDI isocyanate.

TABLE XI

| PHYSICAL PROPERTIES FOR MDI FOAM WITH INDEX 105 | | | | | |
|---|---|---|---|---|---|
| Property | Units | Conditioning | Method | Foam 1 | Foam 2 |
| Tensile Strength | kPa | Ambient | DIN 53571 | 140 | 142 |
| Tensile Elongation | % | Ambient | DIN 53571 | 97 | 92 |
| HA Tensile Strength | kPa | Volkswagen | DIN 53571 | 119 | 94 |
| HA Tensile Elongation | % | Volkswagen | DIN 53571 | 108 | 113 |
| 50% Compression Set | % | Ambient | ASTM 3574-D | 6.1 | 6.5 |
| 50% HA Compression Set | % | Volkswagen | ASTM 3574-D | 31 | 31 |
| CLD | kPa | Ambient | ASTM 3574-D | 10 | 11 |
| HA CLD | kPa | Volkswagen | ASTM 3574-D | 8.5 | 8 |
| HALLS | % | Volkswagen | ISO-3386-1 | −13 | −26 |

While the invention has been described with reference to certain aspects or embodiments, it will be understood by those skilled in the art that various changes may be made and equivalents may be substituted for elements thereof without departing from the scope of the invention. In addition, many modifications may be made to adapt the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for making a low emissions polyurethane foam comprising contacting at least one polyol and at least one polyisocyanate in the presence of a catalyst composition comprising a combination of a gelling catalyst and at least one blowing catalyst, wherein the gelling catalyst consists of N,N-bis(dimethylaminopropyl)-N-(3-aminopropyl)-amine, wherein the at least one blowing catalyst comprises N,N,N'-trimethyl-N'-3-aminopropyl-bis(aminoethyl) ether; wherein the amount of N,N-bis(dimethylaminopropyl)-N-(3-aminopropyl)-amine in the polyurethane foam is about 0.1 to about 5 parts by weight per hundred parts by weight of the at least one polyol, and wherein the amount of N,N,N'-trimethyl-N'-3-aminopropyl-bis(aminoethyl) ether in the polyurethane foam is about 0.01 to about 5 parts by weight per hundred parts by weight of the at least one polyol.

2. The method of claim 1 wherein the polyisocyanate has an NCO index of about 60 to 65.

3. The method of claim 1 wherein the polyisocyanate has an NCO index of about 90 to 110.

4. The method of claim 1 wherein the catalyst composition further comprises at least one additional blowing catalyst other than N,N,N'-trimethyl-N'-3-aminopropyl-bis(aminoethyl) ether.

5. The method of claim 4 wherein the at least one additional blowing catalyst other than N,N,N'-trimethyl-N'-3-aminopropyl-bis(aminoethyl) ether is a non-emissive tertiary amine.

6. A method for making a low emissions polyurethane foam comprising contacting at least one polyol and at least one polyisocyanate in the presence of a catalyst composition comprising a combination of a gelling catalyst, at least one gelling co-catalyst and at least one blowing catalyst, wherein the gelling catalyst consists of N,N-bis(dimethylaminopropyl)-N-(3-aminopropyl)-amine, wherein the gelling co-catalyst is selected from the group consisting of N,N-bis(3-dimethylamino-propyl)-N-(2-hydroxypropyl) amine; N,N-dimethyl-N',N'-bis(2-hydroxypropyl)-1,3-propylenediamine; dimethylaminopropylamine; N-methyl-N-2-hydroxypropyl-piperazine, bis-dimethylaminopropyl amine, dimethylaminopropyl urea, N,N'-bis(3-dimethylaminopropyl) urea, 1,3-bis(dimethylamino)-2-propanol, 6-dimethylamino-1-hexanol, N-(3-aminopropyl)imidazole, N-(2-hydroxypropyl)imidazole, N,N'-bis(2-hydroxypropyl) piperazine, N-(2-hydroxypropyl)-morpholine, and N-(2-hydroxyethylimidazole), wherein the at least one blowing catalyst comprises N,N,N'-trimethyl-N'-3-aminopropyl-bis(aminoethyl) ether; and wherein the amount of N,N-bis(dimethylaminopropyl)-N-(3-aminopropyl)-amine in the polyurethane foam is about 0.1 to about 5 parts by weight per hundred parts by weight of the at least one polyol.

7. The method of claim 6 wherein the polyisocyanate has an NCO index of about 60 to 65.

8. The method of claim 6 wherein the polyisocyanate has an NCO index of about 90 to 110.

9. The method of claim 6 wherein the catalyst composition further comprises at least one additional blowing catalyst other than N,N,N'-trimethyl-N'-3-aminopropyl-bis(aminoethyl) ether.

10. The method of claim 9 wherein the at least one additional blowing catalyst other than N,N,N'-trimethyl-N'-3-aminopropyl-bis(aminoethyl) ether is a non-emissive tertiary amine.

* * * * *